US012655079B2

(12) United States Patent
Simanzhenkov et al.

(10) Patent No.: US 12,655,079 B2
(45) Date of Patent: Jun. 16, 2026

(54) FEED PURIFICATION IN ETHANE ODH PROCESS

(71) Applicant: NOVA CHEMICALS (INTERNATIONAL) S.A., Fribourg (CH)

(72) Inventors: Vasily Simanzhenkov, Calgary (CA); Shahin Goodarznia, Calgary (CA); Bolaji Olayiwola, Calgary (CA); Jeffrey Kluthe, Lacombe (CA)

(73) Assignee: NOVA CHEMICALS (INTERNATIONAL) S.A., Fribourg (CH)

( * ) Notice: Subject to any disclaimer, the term of this patent is extended or adjusted under 35 U.S.C. 154(b) by 191 days.

(21) Appl. No.: 18/682,200

(22) PCT Filed: Jul. 28, 2022

(86) PCT No.: PCT/IB2022/057015
§ 371 (c)(1),
(2) Date: Feb. 8, 2024

(87) PCT Pub. No.: WO2023/021350
PCT Pub. Date: Feb. 23, 2023

(65) Prior Publication Data
US 2024/0336544 A1     Oct. 10, 2024

Related U.S. Application Data

(60) Provisional application No. 63/235,503, filed on Aug. 20, 2021.

(51) Int. Cl.
*C07C 5/48*     (2006.01)
*B01J 23/00*    (2006.01)

(52) U.S. Cl.
CPC ............... *C07C 5/48* (2013.01); *B01J 23/002* (2013.01); *B01J 2523/55* (2013.01);
(Continued)

(58) Field of Classification Search
CPC ... C07C 5/48; C07C 2523/20; C07C 2523/22; C07C 2523/28; C07C 2523/32;
(Continued)

(56) References Cited

U.S. PATENT DOCUMENTS 9,550,709 B2 * 1/2017 Simanzhenkov ...... B01J 8/0453
2010/0256432 A1 * 10/2010 Arnold ...................... C07C 5/48
585/655

(Continued)

FOREIGN PATENT DOCUMENTS

WO     WO 2005/061092     7/2005
WO     WO 2014/138520 B2     9/2014

OTHER PUBLICATIONS

International Search Report and Written Opinion issued in corresponding International application PCT/IB2022/057015 mailed Nov. 16, 2022.

*Primary Examiner* — Ellen M McAvoy
(74) *Attorney, Agent, or Firm* — NORTON ROSE FULBRIGHT US LLP

(57)     ABSTRACT

A feed stream including ethane is flowed to a purification unit that includes a first oxidative dehydrogenation catalyst. The feed stream is contacted with the first oxidative dehydrogenation catalyst at a first temperature to reduce a concentration of impurities in the feed stream to produce a purified feed stream. The purified feed stream is flowed to an oxidative dehydrogenation unit that includes a second oxidative dehydrogenation catalyst. The purified feed stream is contacted with the second oxidative dehydrogenation catalyst in the presence of oxygen at a second temperature
(Continued)

greater than the first temperature to dehydrogenate ethane to produce a product stream that includes ethylene.

12 Claims, 6 Drawing Sheets

(52) U.S. Cl.
  CPC ........ *B01J 2523/56* (2013.01); *B01J 2523/64* (2013.01); *B01J 2523/68* (2013.01); *C07C 2523/20* (2013.01); *C07C 2523/22* (2013.01); *C07C 2523/28* (2013.01); *C07C 2523/32* (2013.01)

(58) Field of Classification Search
  CPC .. C07C 7/148; C07C 2527/057; B01J 23/002; B01J 2523/55; B01J 2523/56; B01J 2523/64; B01J 2523/68
  See application file for complete search history.

(56) References Cited

U.S. PATENT DOCUMENTS

| | | | | |
|---|---|---|---|---|
| 2017/0226030 A1* | 8/2017 | Li | .............................. | C07C 5/42 |
| 2019/0248717 A1* | 8/2019 | Gaffney | .............. | B01J 19/2415 |
| 2020/0223768 A1* | 7/2020 | Van Rossum | ............. | C07C 5/48 |
| 2020/0239396 A1* | 7/2020 | Zellhuber | ................. | C07C 5/48 |
| 2022/0323942 A1* | 10/2022 | Gao | ........................ | B01J 37/033 |
| 2023/0303466 A1* | 9/2023 | Goodarznia | .............. | C07C 5/48 |
| 2023/0357108 A1* | 11/2023 | Goodarznia | .............. | C07C 5/48 |
| 2024/0336544 A1* | 10/2024 | Simanzhenkov | ...... | B01J 23/002 |
| 2024/0368058 A1* | 11/2024 | Olayiwola | .......... | C07C 7/14891 |

* cited by examiner

Flow Feed Stream to Purification Unit — 302

Contact Feed Stream with 1ˢᵗ Catalyst to Produce Purified Feed Stream — 304

Flow Purified Feed Stream to Oxidative Dehydrogenation Unit — 306

Contact Purified Feed Stream with 2ⁿᵈ Catalyst to Produce Product Stream — 308

300

400

FEED PURIFICATION IN ETHANE ODH PROCESS

CROSS-REFERENCE TO RELATED APPLICATION

This application is a national phase application under 35 U.S.C. § 371 of International Application No. PCT/IB2022/057015, filed Jul. 28, 2022, which claims priority to and the benefit of U.S. Provisional Application No. 63/235,503, filed Aug. 20, 2021. The contents of the referenced patent applications are incorporated into the present application by reference.

TECHNICAL FIELD

The present specification is directed to an oxidative dehydrogenation process to convert ethane to ethylene. More specifically, an oxidative dehydrogenation process which includes purifying the feed stream is described.

BACKGROUND ART

Oxidative dehydrogenation of ethane using mixed metal oxide catalysts is an alternative to steam cracking for the production of ethylene. Oxidative dehydrogenation of ethane is a way of converting ethane, which is relatively inert, into ethylene, which is more reactive and can be more valuable. Oxidative dehydrogenation of ethane involves the endothermic removal of hydrogen from ethane and the exothermic oxidation of hydrogen to produce water.

Impurities in a feed stream for an oxidative dehydrogenation process can accumulate on the surface of an oxidative dehydrogenation catalyst over time, which can affect conversion of ethane and in turn, yield of ethylene. Some examples of impurities can include boron, sodium, and green oil. It can be beneficial to purify the feed stream to remove such impurities before it undergoes the oxidative dehydrogenation process.

SUMMARY OF INVENTION

Certain aspects of the subject matter described can be implemented as a process for oxidative dehydrogenation of ethane. A feed stream including ethane is flowed to a purification unit that includes a first oxidative dehydrogenation catalyst. The feed stream is contacted with the first oxidative dehydrogenation catalyst at a first temperature to reduce a concentration of impurities in the feed stream to produce a purified feed stream. The purified feed stream is flowed to an oxidative dehydrogenation unit that includes a second oxidative dehydrogenation catalyst. The purified feed stream is contacted with the second oxidative dehydrogenation catalyst at a second temperature greater than the first temperature to dehydrogenate ethane to produce a product stream that includes ethylene. This, and other aspects, can include one or more of the following features.

In some embodiments, the first temperature is less than about 250 degrees Celsius (° C.). In some embodiments, the second temperature is greater than about 300° C. In some embodiments, the first oxidative dehydrogenation catalyst and the second oxidative dehydrogenation catalyst have the same composition. In some embodiments, the first oxidative dehydrogenation catalyst and the second oxidative dehydrogenation catalyst have different compositions. In some embodiments, the purification unit operates adiabatically.

In some embodiments, the purification unit includes a first purification bed and a second purification bed in a parallel flow configuration. In some embodiments, a first portion of the first oxidative dehydrogenation catalyst is disposed within the first purification bed, and a second portion of the first oxidative dehydrogenation catalyst is disposed within the second purification bed. In some embodiments, flowing the feed stream to the purification unit includes flowing the feed stream to the first purification bed. In some embodiments, contacting the feed stream with the first oxidative dehydrogenation catalyst includes contacting the feed stream with the first portion of the first oxidative dehydrogenation catalyst disposed within the first purification bed.

In some embodiments, the second portion of the first oxidative dehydrogenation catalyst disposed within the second purification bed is regenerated while the feed stream is flowed to the first purification bed. In some embodiments, regenerating the second portion of the first oxidative dehydrogenation catalyst includes contacting the second portion of the first oxidative dehydrogenation catalyst with acetic acid. In some embodiments, the product stream includes acetic acid. In some embodiments, the acetic acid is separated from the product stream. In some embodiments, acetic acid separated from the product stream is recycled to the second purification bed. In some embodiments, the second portion of the first oxidative dehydrogenation catalyst disposed within the second purification bed is contacted with the recycled acetic acid. In some embodiments, an oxidizing stream including oxygen is flowed to the second purification bed while the feed stream is flowed to the first purification bed. In some embodiments, the acetic acid is dilute aqueous acetic acid (for example, acetic acid diluted with steam).

Certain aspects of the subject matter described can be implemented as a system for oxidative dehydrogenation of ethane. The system includes a feed stream, a purification unit, and an oxidative dehydrogenation unit. The feed stream includes ethane. The purification unit includes a first oxidative dehydrogenation catalyst. The first oxidative dehydrogenation catalyst is configured to reduce a concentration of impurities in the feed stream in response to contacting the feed stream at a first temperature to produce a purified feed stream. The oxidative dehydrogenation unit is downstream of the purification unit. The oxidative dehydrogenation unit includes a second oxidative dehydrogenation catalyst. The second oxidative dehydrogenation catalyst is configured to dehydrogenate ethane in response to contacting the purified feed stream in the presence of oxygen at a second temperature greater than the first temperature to produce a product stream comprising ethylene. This, and other aspects, can include one or more of the following features.

In some embodiments, the first temperature is less than about 250 degrees Celsius (° C.). In some embodiments, the second temperature is greater than about 300° C. In some embodiments, the first oxidative dehydrogenation catalyst and the second oxidative dehydrogenation catalyst have the same composition. In some embodiments, the first oxidative dehydrogenation catalyst and the second oxidative dehydrogenation catalyst have different compositions.

In some embodiments, the purification unit includes a first purification bed and a second purification bed in a parallel flow configuration. In some embodiments, a first portion of the first oxidative dehydrogenation catalyst is disposed within the first purification bed, and a second portion of the first oxidative dehydrogenation catalyst is disposed within the second purification bed.

In some embodiments, the product stream includes acetic acid. In some embodiments, the system includes a separation unit downstream of the oxidative dehydrogenation unit. In some embodiments, the separation unit is configured to separate the acetic acid from the product stream. In some embodiments, the system includes a recycle flowline configured to recycle the acetic acid (separated from the product stream) to the second purification bed, thereby contacting the second portion of the first oxidative dehydrogenation catalyst with the recycled acetic acid and regenerating the second portion of the first oxidative dehydrogenation catalyst. In some embodiments, the acetic acid is dilute aqueous acetic acid (for example, acetic acid diluted with steam).

It is understood that the disclosure described in this specification is not limited to the examples summarized in this Summary. Various other aspects are described and exemplified herein.

DESCRIPTION OF EMBODIMENTS

Figure 1A:
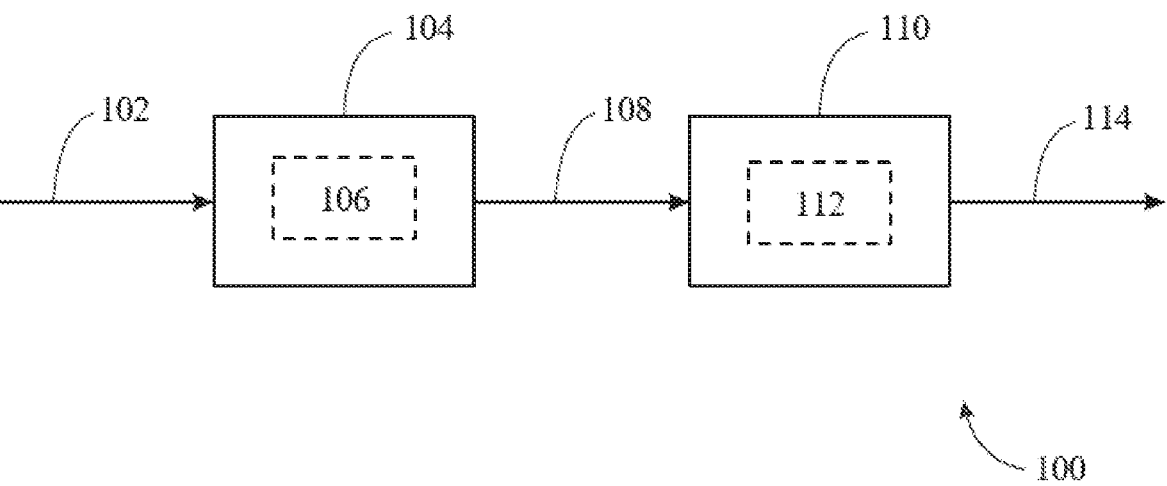
FIG. 1A is a schematic diagram of an example system for oxidative dehydrogenation.

Provided in this disclosure is a process for the oxidative dehydrogenation of ethane. The process includes contacting a feed stream that includes ethane with a first oxidative dehydrogenation catalyst at a first temperature to reduce a concentration of impurities in the feed stream to produce a purified feed stream. The process includes contacting the purified feed stream with a second oxidative dehydrogenation catalyst in the presence of oxygen at a second temperature greater than the first temperature to produce a product stream that includes ethylene. The system 100 of FIG. 1A can implement the oxidative dehydrogenation process. The present disclosure, in one aspect, seeks to purify a feed stream 102 in a process of oxidative dehydrogenation of ethane by including a purification unit 104.

Definitions

As used herein, the term "oxidative dehydrogenation catalyst" refers to catalysts used in the oxidative dehydrogenation of ethane into ethylene. The most frequently described oxidative dehydrogenation catalysts are mixed metal oxide catalysts. Use of the term "catalyst", unless otherwise indicated, is synonymous with oxidative dehydrogenation catalyst. Furthermore, referral to an oxidative dehydrogenation catalyst can include a mixture of more than one oxidative dehydrogenation catalyst, each having different chemical compositions which can be supported or unsupported.

As used herein, the term "feed stream" refers to the gas stream that initially contacts the first oxidative dehydrogenation catalyst. The feed stream in a typical oxidative dehydrogenation process includes the components ethane and oxygen, and possibly one or more inert diluents. In some instances, the contribution of components to the feed stream is described as the "feed composition", where the vol. % of one or more components are stated. In some instances, components within the feed stream, particularly oxygen and ethane, are described using a vol. % ratio.

As used herein, the term "inert diluent" refers to a gaseous composition that is used to dilute the ethane and oxygen to lower the flammability of the mixture. An inert diluent should primarily exist in the gaseous state under oxidative dehydrogenation conditions and should not increase the flammability of the ethane. Common inert diluents known to the person of ordinary skill in the art for oxidative dehydrogenation include, but are not limited to, nitrogen, carbon dioxide, and steam, and mixtures thereof.

As used herein, the term "under oxidative dehydrogenation conditions" refers to the process conditions that permit conversion, through contact with the oxidative dehydrogenation catalyst in the presence of oxygen, of ethane into ethylene, and includes, but is not limited to, temperature, pressure, and the flow rate of the feed stream. Oxidative dehydrogenation conditions can be adjusted by the person of ordinary skill in the art in an attempt to optimize conditions for a particular catalyst or whether an inert diluent is used in the feed stream.

As used herein, the term "selectivity", unless otherwise indicated, refers to the carbon atom selectivity, based on the degree to which ethane is consumed. Selectivity, stated as a %, can be calculated according to the formula:

$$\text{Selectivity (\%)} = \frac{\dfrac{\text{Net mass flow rate of } X(\text{g } X/\text{min})}{\text{Molecular weight of } X(\text{g } X/\text{mol } X)}}{\dfrac{\text{Net mass flow rate of converted } C_2H_6(\text{g } C_2H_6/\text{min})}{\text{Molecular weight of } C_2H_6(\text{g } C_2H_6/\text{mol } C_2H_6)} * \dfrac{\text{Mol. } Equiv. \text{ of } X}{\text{mol } C_2H_6}} * 100$$

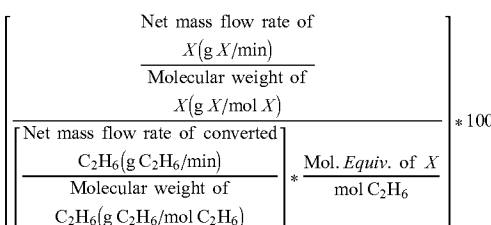

where X is the product that is being assessed, the net mass flow rate refers to flow in g/min for X or equivalent converted $C_2H_6$ and is equal to the mass flow rate of X or converted $C_2H_6$ in the product stream minus the mass flow rate of component X or converted $C_2H_6$ in the feed stream, and molar equivalent (Mol. Equiv.) refers to the amount of X, in moles, that reacts completely with or is produced by one mole of ethane. If the sum of all selectivities for products derived from conversion of ethane did not total 100%, the selectivities are normalized to 100%. Normalization for each product can be calculated by dividing the selectivity for that product by the sum of all carbon atom product selectivities.

As used herein, the term "about" or "approximately" can allow for a degree of variability in a value or range, for example, within 10%, within 5%, or within 1% of a stated value or of a stated limit of a range.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Certain exemplary aspects of the present disclosure will now be described to provide an overall understanding of the principles of the process disclosed herein. Those of ordinary skill in the art will understand that the processes described herein are non-limiting exemplary aspects and that the scope of the various examples of the present disclosure is defined solely by the claims. The features illustrated or described in connection with one exemplary aspect may be combined with the features of other aspects. Such modifications and variations are intended to be included within the scope of the present disclosure.

Embodiments of the present techniques are directed to a process for oxidative dehydrogenation (ODH) of ethane into ethylene that includes purification of the feed stream. Typically, oxidative dehydrogenation of ethane involves feeding a gas stream including ethane and oxygen, and optionally an inert diluent, into an oxidative dehydrogenation reactor that includes an oxidative dehydrogenation catalyst. Contact of the ethane and oxygen with the oxidative dehydrogenation catalyst results in the formation of ethylene. It is an object of the present disclosure to purify the feed stream before the feed stream undergoes oxidative dehydrogenation. Purification of the feed stream can mitigate and/or prevent premature deactivation of the oxidative dehydrogenation catalyst. Further, it is an object of the present disclosure to re-use spent catalyst to perform the purification of the feed stream as a way to implement cost savings in the oxidative dehydrogenation process.

Feed Composition

The feed stream 102 includes ethane. In some implementations, the feed stream 102 also includes oxygen, acetic acid, an inert diluent (for example, nitrogen, carbon dioxide, and steam), or a combination of these. The feed stream preferably includes an oxygen to ethane ($O_2:C_2H_6$) ratio that falls outside of flammability limits to prevent process upsets. A user can determine how much inert diluent can be added to ensure the mixture is outside the flammability limits. It should be noted that a feed stream 102 without an inert diluent, while possible, would not be ideal as to remain outside the flammability limit the feed stream would require an $O_2:C_2H_6$ ratio that is very small or extremely high. Use of steam as an inert diluent provides the advantage of being simpler to separate from the gaseous target products, but is known to also increase selectivity to acetic acid.

In some embodiments, the $O_2:C_2H_6$ volume ratio in the feed stream 102 is from 0.2:1 to 1:1, from 0.3:1 to 0.8:1, or from 0.4:1 to 0.7:1. In some embodiments, the contribution of ethane in the feed stream 102 is from 10 vol. % to 80 vol. %, from 12 vol. % to 50 vol. %, or from 15 vol. % to 30 vol. %. In some embodiments, the contribution of oxygen in the feed stream 102 is from 1 vol. % to 30 vol. %, from 5 vol. % to 25 vol. %, or from 8 vol. % to 18 vol. %.

The components of the feed stream 102 can be premixed before introduction into the purification unit 104 or the components may be added separately to the purification unit 104. It is also contemplated that some components are premixed and some components are separately fed to the purification unit 104. For example, ethane can be combined with the inert diluent and introduced into the purification unit 104 while the oxygen is added separately. The ethane combined with the inert diluent can then be combined with the oxygen to form the feed stream 102 that contacts the first oxidative dehydrogenation catalyst 106. The process described also contemplates staged additions of components into a gas stream, each stage contributing another component to the gas stream with the feed stream 102 being formed after the last component is added.

The acetic acid may be added separately to the oxidative dehydrogenation reactor 104 or may be mixed with one or more of the ethane, oxygen, or inert diluent. Acetic acid may be added as glacial acetic acid or in a diluted form to provide acetic acid in amounts ranging from about 0.5 to 10.0 vol. % of the feed stream 102. For example, the acetic acid can be diluted with water. Use of dilute aqueous acetic acid is ideal, as water is well known as being suitable for use as the inert diluent in the oxidative dehydrogenation process.

The feed stream 102 can be heated, at a minimum, to a temperature above the dew point of the feed stream 102 to ensure all components are in a gaseous state before making contact with the first oxidative dehydrogenation catalyst 106 disposed within the purification unit 104. This is particularly relevant when water is employed as inert diluent because the first oxidative dehydrogenation catalyst 106 may be sensitive to liquid water, but not steam. For example, the presence of liquid water may introduce the risk of catalyst particle pulverization due to evaporation of the liquid water. In some embodiments, the steam in the system 100 (for example, included in the feed stream 102 and/or included in the dilute aqueous acetic acid) is saturated steam. In some embodiments, the steam in the system 100 is superheated steam. The components may be heated separately or as a complete mixture. In some embodiments, the temperature of the feed stream 102 is at least 150° C. or at least 225° C.

The temperature of the feed stream 102, or individual components, upon entering the purification unit 104 may be lower than 150° C., provided that before contact with the catalyst in the purification unit 104, the temperature is increased to above the dew point of the feed stream 102. In some embodiments, a portion of the purification unit 104 may be used to heat the feed stream 102 components to the preferred temperature. This portion of the catalyst bed may be loaded with heat conductive non-catalytic material.

Purification Unit

The purification unit 104 receives the feed stream 102. The purification unit 104 includes a first oxidative dehydrogenation catalyst 106. The first oxidative dehydrogenation catalyst 106 is configured to reduce a concentration of impurities in the feed stream 102 in response to contacting the feed stream 102 at a first temperature to produce a purified feed stream 108. For example, as the feed stream 102 flows across the first oxidative dehydrogenation catalyst 106, the impurities from the feed stream 102 can be disposed on the first oxidative dehydrogenation catalyst 106 to produce the purified feed stream 108. In some embodiments, the purified feed stream 108 has a boron (B) content of less than about 5 volume percent (vol. %), less than about 4 vol. %, less than about 3 vol. %, less than about 2 vol. %, or less than about 1 vol. %. In some embodiments, the purified feed stream 108 has a sodium (Na) content of less than about 5 vol. %, less than about 4 vol. %, less than about 3 vol. %, less than about 2 vol. %, or less than about 1 vol. %. In some embodiments, the B content in the feed stream 102 is reduced by about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or about 5% to produce the purified feed stream 102. In some embodiments, the Na content in the feed stream 102 is reduced by about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or about 5% to produce the purified feed stream 102. In some embodiments, the first temperature is less than about 250° C., such that undesired side reactions are avoided.

Any of a number of reactor types applicable for the purification of the feed stream 102 can be used with the present techniques. For example, fixed bed reactors, fluidized bed reactors, or a combination of both may be used, among others. Particularly suited for use are conventional fixed bed reactors. In a typical fixed bed reactor, reactants are introduced into the reactor at one end, flow past an immobilized catalyst, products are formed and leave at the other end of the reactor. Designing a suitable fixed bed reactor may follow techniques known for reactors of this type. A person skilled in the art would know which features are required with respect to shape and dimensions, inputs for reactants, outputs for products, temperature and pressure control, and means for immobilizing the catalyst. In some embodiments, the purification unit 104 includes a fixed bed reactor. Fluidized bed reactors can also be used. These types of reactors are also well known. Typically, the catalyst is supported by a porous structure, or distributor plate, located near a bottom end of the reactor, and reactants flow through at a velocity sufficient to fluidize the bed (e.g., the catalyst rises and begins to swirl around in a fluidized manner). The reactants are converted to products upon contact with the fluidized catalyst and subsequently removed from the upper end of the reactor. Design considerations include shape of the reactor and distributor plate, input and output, and temperature and pressure control, all of which would fall under knowledge of the person skilled in the art. In some embodiments, the purification unit 104 includes a fluidized bed reactor.

Oxidative Dehydrogenation Unit

An oxidative dehydrogenation unit 110 is downstream of the purification unit 104. The oxidative dehydrogenation unit 110 receives the purified feed stream 108. The oxidative dehydrogenation unit 110 includes a second oxidative dehydrogenation catalyst 112. The second oxidative dehydrogenation catalyst 112 is configured to dehydrogenate ethane (in the purified feed stream 108) in response to contacting the purified feed stream 108 in the presence of oxygen at a second temperature to produce a product stream 114 that includes ethylene. The second temperature at which the oxidative dehydrogenation unit 110 operates is greater than the first temperature at which the purification unit 104 operates. In some embodiments, the second temperature is greater than about 300° C.

Any of the known reactor types applicable for the oxidative dehydrogenation of hydrocarbons can be used with the present techniques. For example, fixed bed reactors, fluidized bed reactors, or a combination of both may be used. In some embodiments, the oxidative dehydrogenation unit 110 includes a fixed bed reactor. In some embodiments, the oxidative dehydrogenation unit 110 includes a shell-and-tube type reactor. In some embodiments, the oxidative dehydrogenation unit 110 includes a fluidized bed reactor. In some embodiments the oxidative dehydrogenation unit may comprise multiple reactors in series or parallel configuration.

Various tools commonly used for chemical reactors, including flowmeters, compressors, valves, and sensors for measuring parameters such as temperature and pressure can be used. It is expected that the person of ordinary skill in the art would include these components as deemed necessary for operation or for compliance with legal obligations related to safety regulations.

Process Conditions

Use of an oxidative dehydrogenation reactor for performing an oxidative dehydrogenation of ethane process consistent with the present disclosure falls within the knowledge of the person skilled in the art. An operator may alter the process conditions, along with the feed composition, to optimize product selectivity, conversion, and or yield.

It is well known that catalyst beds may have a temperature profile or gradient that can vary according to reactor type, process conditions and catalyst composition. Measuring or estimating the temperature of the catalyst bed is also well known in the art, including measuring the temperature at single or multiple points within the catalyst bed. If the variation of temperature within the catalyst bed is minimal, ranging no more than 25° C., preferably no more than 10° C., the temperature may be measured at a single point. Preferably, the temperature of the catalyst is calculated using a weight-averaged bed temperature using 3 or more points within the bed. In some embodiments, the oxidative dehydrogenation of ethane may be conducted at temperatures from 300° C. to 550° C., 300° C. to 500° C., 300° C. to 450° C., from 315° C. to 425° C., or from 330° C. to 400° C. In some embodiments, the oxidative dehydrogenation of ethane may be conducted at temperatures of about 300° C., about 315° C., about 330° C., about 400° C., about 425° C., about 450° C., about 500° C., or about 550° C.

Operating pressure may also be controlled by an operator, including the inlet pressure at which the feed stream is introduced into the oxidative dehydrogenation reactor, the inlet pressure being higher than the outlet pressure due to a pressure drop through the length of the catalyst bed. Pressures described are for inlet pressure. In some embodiments, the oxidative dehydrogenation of ethane may be conducted at pressures from 0.5 to 100 psig (3.447 to 689.47 kPag) or from 15 to 50 psig (103.4 to 344.73 kPag). In some embodiments, the oxidative dehydrogenation of ethane may be conducted at pressures of about 0.5 psig, about 10 psig, about 15 psig, about 20 psig, about 30 psig, about 50 psig, about 75 psig, or about 100 psig.

The pressure drop through the length of the catalyst bed depends on several factors, including, but not limited to, the catalyst bed configuration, including the size and shape of catalyst particles, the process conditions, and the size of the reactor. Larger reactors are associated with a greater pressure drop along the length of the catalyst bed. In some embodiments, the pressure drop along the length of the catalyst bed is between 0.1 and 50 psig.

In some embodiments, the residence time of the ethane in the reactor is from 0.12 to 7.2 seconds or from 0.18 to 3.6 seconds. In some embodiments, the residence time of the ethane in the reactor is about 0.12 seconds, about 0.5 seconds, about 1 seconds, about 3 seconds, about 4 seconds, about 5 seconds, about 6 seconds, and about 7.2 seconds. The flow of reactants and inert diluent can be described in any number of ways known in the art.

Typically, flow is described and measured in relation to the volume of all feed gases (reactants and diluent) that pass over the volume of the active catalyst bed in one hour, or gas hourly space velocity (GHSV). In some embodiments, the GHSV is from 500 to 30000 h$^{-1}$, from 1000 h$^{-1}$ to 20000 h$^{-1}$, from 1500 h$^{-1}$ to 10000 h$^{-1}$, or from 2000 h$^{-1}$ to 10000 h$^{-1}$. In some embodiments, the GHSV is about 500 h$^{-1}$, about 1000 h$^{-1}$, about 1500 h$^{-1}$, about 2000 h$^{-1}$, about 3000 h$^{-1}$, about 4000 h$^{-1}$, about 5000 h$^{-1}$, about 6000 h$^{-1}$, about 7000 h$^{-1}$, about 8000 h$^{-1}$, about 9000 h$^{-1}$, about 10000 h$^{-1}$, about 15000 h$^{-1}$, about 20000 h$^{-1}$, about 25000 h$^{-1}$, or about 30000 h$^{-1}$.

The flow rate can also be measured as weight hourly space velocity (WHSV), which describes the flow in terms of the weight, as opposed to volume, of the gases that flow over the weight of the active catalyst per hour. In calculating WHSV the weight of the gases may include only the reactants but may also include diluents added to the gas mixture. As WHSV decreases, pressure drop across the reactor decreases. As WHSV increases, pressure drop across the reactor increases. To achieve the same ethylene production, the reactor size increases as WHSV decreases. To achieve the same ethylene production, the reactor size can decrease as WHSV increase. On the other hand, if the reactor size is fixed, then the ethylene production decreases as WHSV decreases, and the ethylene production increases as WHSV increases. As WHSV decreases, there is an increased chance of hot spots forming in the reactor. As WHSV increases, there is a decreased chance of hot spots forming in the reactor. Implementing a WHSV within the following ranges can balance such effects. In some embodiments, the WHSV, including the weight of diluents, is from 0.5 h$^{-1}$ to 50 h$^{-1}$, from 1.0 to 25.0 h$^{-1}$, or from 2.0 to 10.0 h$^{-1}$. In some embodiments, the WHSV, including the weight of diluents, is about 0.5 h$^{-1}$, about 1.0 h$^{-1}$, about 1.5 h$^{-1}$, about 2.0 h$^{-1}$, about 3.0 h$^{-1}$, about 4.0 h$^{-1}$, about 5.0 h$^{-1}$, about 6.0 h$^{-1}$, about 7.0 h$^{-1}$, about 8.0 h$^{-1}$, about 9.0 h$^{-1}$, about 10 h$^{-1}$, about 15 h$^{-1}$, about 20 h$^{-1}$, about 25 h$^{-1}$, about 30 h$^{-1}$, about 40 h$^{-1}$, or about 50 h$^{-1}$.

The flow of the purified feed stream 108 through the oxidative dehydrogenation unit 110 may also be described as the linear velocity of the feed stream (cm/s), which is defined in the art as the flow rate of the feed stream 108/cross-sectional surface area of the reactor/void fraction of the catalyst bed. The flow rate, at standard conditions for temperature and pressure (STP), generally means the total of the flow rates of all the gases entering the reactor, and is measured where the oxygen and alkane first contact the catalyst and at the temperature and pressure at that point. The cross-section of the reactor is also measured at the entrance of the catalyst bed. The void fraction of the catalyst bed is defined as the volume of voids in the catalyst bed/total volume of the catalyst bed. The volume of voids refers to the voids between catalyst particles and does not include the volume of pores inside the catalyst particles. The effects of linear velocity of the flow rate is similar to the effects of WHSV. As linear velocity decreases, pressure drop across the reactor decreases. As linear velocity increases, pressure drop across the reactor increases. Implementing a linear velocity within the following ranges can balance such effects. In some embodiments, the linear velocity is from 5 cm/sec to 1500 cm/sec, from 10 cm/sec to 500 cm/sec, or from 25 cm/sec to 350 cm/sec. In some embodiments, the linear velocity is about 5 cm/sec, about 10 cm/sec, about 15 cm/sec, about 20 cm/sec, about 25 cm/sec, about 50 cm/sec, about 75 cm/sec, about 100 cm/sec, about 150 cm/sec, about 200 cm/sec, about 250 cm/sec, about 300 cm/sec, about 350 cm/sec, about 400 cm/sec, about 500 cm/sec, about 600 cm/sec, about 700 cm/sec, about 800 cm/sec, about 900 cm/sec, about 1000 cm/sec, about 1250 cm/sec, or about 1500 cm/sec. In some embodiments, the space-time yield of ethylene (productivity) in g of ethylene/hour per kg of the catalyst is at least 900 h$^{-1}$ or at least 1500 h$^{-1}$. In some embodiments, the space-time yield of ethylene (productivity) in g of ethylene/hour per kg of the catalyst is at least 3500 h$^{-1}$, when the temperature is from 350° C. to 400° C.

It should be noted that the increased productivity of the catalyst with increasing temperature is usually accompanied by a decrease in selectivity to ethylene.

Optimization or adjustment of the process conditions can impact the conversion rates of ethane and corresponding selectivities, including selectivity for ethylene and acetic acid. In some embodiments, the process has a selectivity for ethylene of at least 60%, at least 75%, at least 90%, or at least 94%. In some embodiments, the conversion of ethane is at least 25%, at least 40%, at least 50%, at least 60%, or at least 70%.

Oxidative Dehydrogenation Catalysts There are a number of known catalysts which may be used in the oxidative dehydrogenation of ethane. Mixed metal oxides including molybdenum and vanadium are particularly well suited for implementation in the catalyst. In some embodiments, the first oxidative dehydrogenation catalyst 106 and the second oxidative dehydrogenation catalyst 112 have the same composition. In some embodiments, the first oxidative dehydrogenation catalyst 106 and the second oxidative dehydrogenation catalyst 112 have different compositions. In some embodiments, the first oxidative dehydrogenation catalyst 106 is fresh catalyst (that is, catalyst that is new for first use in an oxidative dehydrogenation process). In some embodiments, the first oxidative dehydrogenation catalyst 106 is spent catalyst (that is, catalyst that has already been used in an oxidative dehydrogenation process and no longer exhibits the necessary activity or specificity required by the operator).

Typically, the oxidative dehydrogenation catalysts (106, 112) comprise a mixed metal oxide catalysts selected from the group consisting of:

i) catalysts of the formula:

$$Mo_aV_bTe_cNb_dPd_eO_f$$

wherein a, b, c, d, e and f are the relative atomic amounts of the elements Mo, V, Te, Nb, Pd and O, respectively; and when a=1, b=0.01 to 1.0 preferably 0.1 to 0.4, c=0.01 to 1.0 preferably 0.1 to 0.3, d=0.01 to 1.0 preferably 0.1 to 0.3, 0.00≤e≤0.10 preferably from 0.03 to 0.1 and f is a number to satisfy the valence state of the catalyst;

ii) catalysts of the formula:

$$Mo_aE_kG_lO_f$$

wherein: E is selected from the group consisting of Ba, Ca, Cr, Mn, Nb, Ta, Ti, Te, V, W and mixtures thereof; G is selected from the group consisting of Bi, Ce, Co, Cu, Fe, K, Mg, V, Ni, P, Pb, Sb, Si, Sn, Ti, U, and mixtures thereof; a=1; k is 0 to 2, preferably 0.2 to 0.6; 1=0 to 2, preferably 0.2 to 0.6, with the proviso that the total value of 1 for Co, Ni, Fe and mixtures thereof is less than 0.5; and f is a number to satisfy the valence state of the catalyst;

iii) catalysts of the formula:

$$V_mMo_nNb_oTe_pMe_qO_f$$

wherein: Me is a metal selected from the group consisting of Ta, Ti, W, Hf, Zr, Sb and mixtures thereof; m is from 0.1 to 3, in some instances from 0.5 to 1; n is from 0.5 to 1.5, in some instances from 0.5 to 1; o is from 0.001 to 3 in some instances from 0.01 to 1; p is from 0.001 to 5 in some instances from 0.01 to 1; q is from 0 to 2 in some instances from 0.01 to 1; and f is a number to satisfy the valence state of the catalyst; and iv) catalysts of the formula:

$$Mo_aV_rX_sZ_uM_vO_f$$

wherein: X is at least one of Nb and Ta; Z is at least one of Te, Ga, Pd, W, Bi and Al, in some embodiments Te, Pd, W, and Bi; M is at least one of Fe, Co, Cu, Cr, Ti, Ce, Zr, Mn, Pb, Mg, Sn, Pt, Si, La, K, Ag and In in some instances Fe, Co, Cu, Cr, Ti, Ce, Zr, Mn, Mg, Sn, Pt, La, Ag and In; a=1.0 (normalized); r=0.05 to 1.0 in some embodiments 0.05 to 0.5; s=0.001 to 1.0 in some embodiment 0.01 to 0.4; t=0.001 to 1.0 in some embodiment from 0.01 to 0.4; u=0.001 to 0.5 in some embodiments 0.01 to 0.03; v=0.001 to 0.3 in some embodiments from 0.01 to 0.2; and f is a number to satisfy the valence state of the catalyst.

v) catalysts of the formula:

$$Mo_aTe_yV_vTa_xO_z$$

wherein: a=1.0 (normalized); y is about 0.01 to about 1.0, in some embodiments about 0.1 to about 0.2, about 0.12 to about 0.17, about 0.14 to about 0.18, or about 0.15; v is about 0.01 to about 1.0, in some embodiments about 0.35 to about 0.75, about 0.39 to about 0.49, about 0.45 to about 0.7, or about 0.49; x is about 0.01 to about 1.0, in some embodiments about 0.05 to about 0.15, about 0.05 to about 0.1, about 0.06 to about 0.15, or about 0.07; and z is the number of oxygen atoms necessary to render the catalyst electronically neutral. In some embodiments, the catalyst has the formula $Mo_1Te_{0.01-1.0}V_{0.01-1.0}Ta_{0.01-1.0}$. In some embodiments, the catalyst has the formula $Mo_1Te_{0.12-0.17}V_{0.39-0.49}Ta_{0.06-0.15}$. In some embodiments, the catalyst has the formula $Mo_1Te_{0.15}V_{0.49}Ta_{0.07}$. In some embodiments, the amorphous content of the catalyst is about 30 wt % to about 50 wt %, about 30 wt % to about 40 wt %, about 33 wt % to about 36 wt %, or about 34 wt % to about 35 wt %.

In some embodiments, the catalyst is a catalyst that includes molybdenum, vanadium, tellurium, niobium, and oxygen wherein the molar ratio of molybdenum to vanadium is from 1:0.12 to 1:0.49, the molar ratio of molybdenum to tellurium is from 1:0.01 to 1:0.30, the molar ratio of molybdenum to niobium is from 1:0.01 to 1:0.30, and oxygen is present at least in an amount to satisfy the valency of any present metal oxides.

In some embodiments, the catalyst is a catalyst that includes molybdenum, vanadium, tellurium, niobium, and oxygen wherein the molar ratio of molybdenum to vanadium is from 1:0.20 to 1:0.45, the molar ratio of molybdenum to tellurium is from 1:0.05 to 1:0.25, the molar ratio of molybdenum to niobium is from 1:0.05 to 1:0.25, and oxygen is present at least in an amount to satisfy the valency of any present metal oxides.

In some embodiments, the catalyst is a catalyst that includes molybdenum, vanadium, tellurium, niobium, and oxygen wherein the molar ratio of molybdenum to vanadium is from 1:0.25 to 1:0.40, the molar ratio of molybdenum to tellurium is from 1:0.10 to 1:0.20, the molar ratio of molybdenum to niobium is from 1:0.10 to 1:0.20, and oxygen is present at least in an amount to satisfy the valency of any present metal oxides.

In some embodiments, the catalyst is a catalyst that includes molybdenum, vanadium, tellurium, niobium, and oxygen wherein the molar ratio of molybdenum to vanadium is from 1:0.30 to 1:0.35, the molar ratio of molybdenum to tellurium is from 1:0.13 to 1:0.17, the molar ratio of molybdenum to niobium is from 1:0.12 to 1:0.14, and oxygen is present at least in an amount to satisfy the valency of any present metal oxides.

Figure 1B:
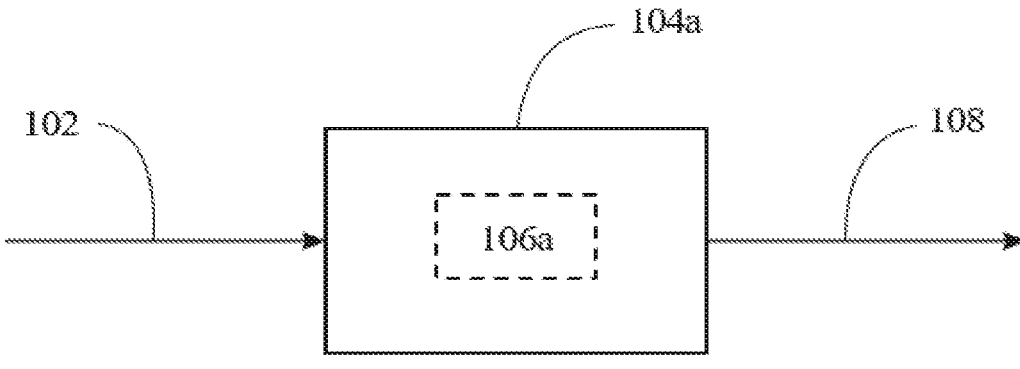
FIG. 1B is a schematic diagram of an example purification unit of the system of FIG. 1A.
Figure 1B:
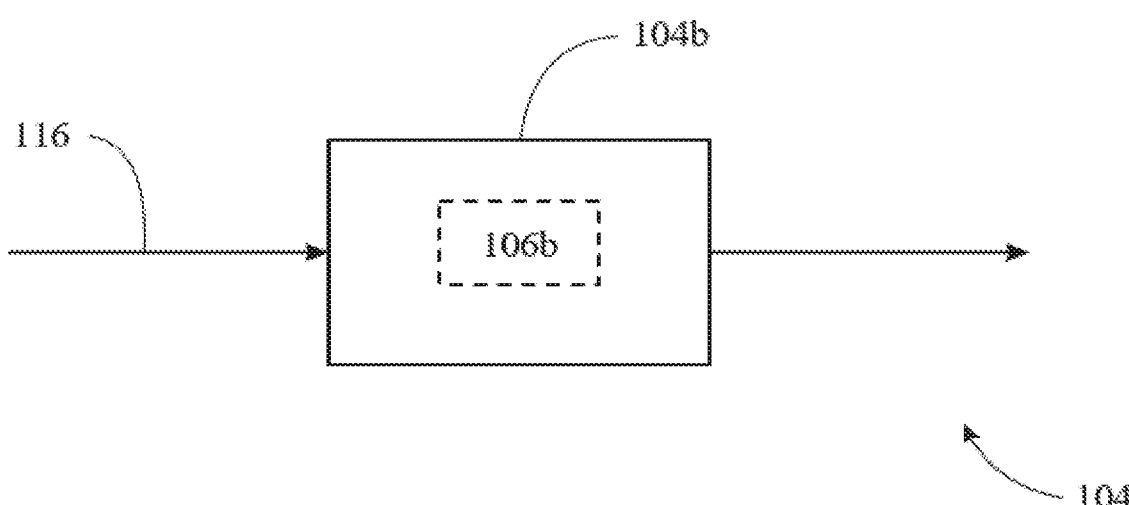

As shown in FIG. 1B, the purification unit 104 can include multiple reactor beds. The reactor beds can be in a parallel flow configuration, a serial flow configuration, or a combination of both. In some embodiments, the purification unit 104 includes a first purification bed 104a and a second purification bed 104b in a parallel flow configuration. In some embodiments, a first portion 106a of the first oxidative dehydrogenation catalyst 106 is disposed within the first purification bed 104a. In some embodiments, a second portion 106b of the first oxidative dehydrogenation catalyst 106 is disposed within the second purification bed 104b.

In some embodiments, one of the purification beds can be used to purify the feed stream 102 while the other is in regeneration mode to regenerate the catalyst. For example, the second portion 106b of the first oxidative dehydrogenation catalyst 106 disposed within the second purification bed 104b can be regenerated while the feed stream 102 is flowed to the first purification bed 104a. For example, the first portion 106a of the first oxidative dehydrogenation catalyst 106 disposed within the first purification bed 104a can be regenerated while the feed stream 102 is flowed to the second purification bed 104b. The modes can be switched, for example, depending on which portion (106a or 106b) of the first oxidative dehydrogenation catalyst 106 needs to be regenerated. This parallel flow configuration allows for the oxidative dehydrogenation process to operate continuously because it eliminates the need to take the system offline to regenerate the catalyst.

Regenerating the first oxidative dehydrogenation catalyst 106, including one or both of the first and second portions 106a and 106b can be done using any means known in the art. In some embodiments, regenerating the first oxidative dehydrogenation catalyst 106 can include contacting the first oxidative dehydrogenation catalyst 106 with acetic acid or dilute aqueous acetic acid (for example, acetic acid diluted with steam). Regeneration can be performed for about 1 hour to up to 24 hours. Alternatively, regeneration can proceed based on the composition of the effluent, with regeneration complete when contaminant levels in the effluent are below a desired level. When using acetic acid or dilute acetic acid for regeneration it is essential that once regeneration is complete that a clean drying gas (e.g. $N_2$, $CO_2$) is passed over the first oxidative dehydrogenation catalyst at a temperature below water boiling at the process pressure to prevent water within the first oxidative dehydrogenation catalyst from pulverizing the catalyst upon vaporization. Drying is complete when humidity of the drying gas downstream of the purification unit is below 10% of relative humidity.

In some embodiments, as shown in FIG. 1B, the feed stream 102 flows to the first purification bed 104a while an oxidizing stream 116 flows to the second purification bed 104b. The oxidizing stream 116 includes oxygen. In some embodiments, the oxidizing stream 116 includes an inert diluent. In some embodiments, the feed stream 102 flows to the second purification bed 104b while the oxidizing stream 116 flows to the first purification bed 104a. The flow of the feed stream 102 and the oxidizing stream 116 to the first and second purification beds 104a, 104b can be switched as desired, such that one of the beds 104a, 104b remain online while the other bed is regenerated.

Various tools commonly used for chemical reactors, including flowmeters, compressors, valves, and sensors for measuring parameters such as temperature and pressure can be used. It is expected that the person of ordinary skill in the art would include these components as deemed necessary for operation or for compliance with legal obligations related to safety regulations.

Recycling Acetic Acid

Figure 1C:
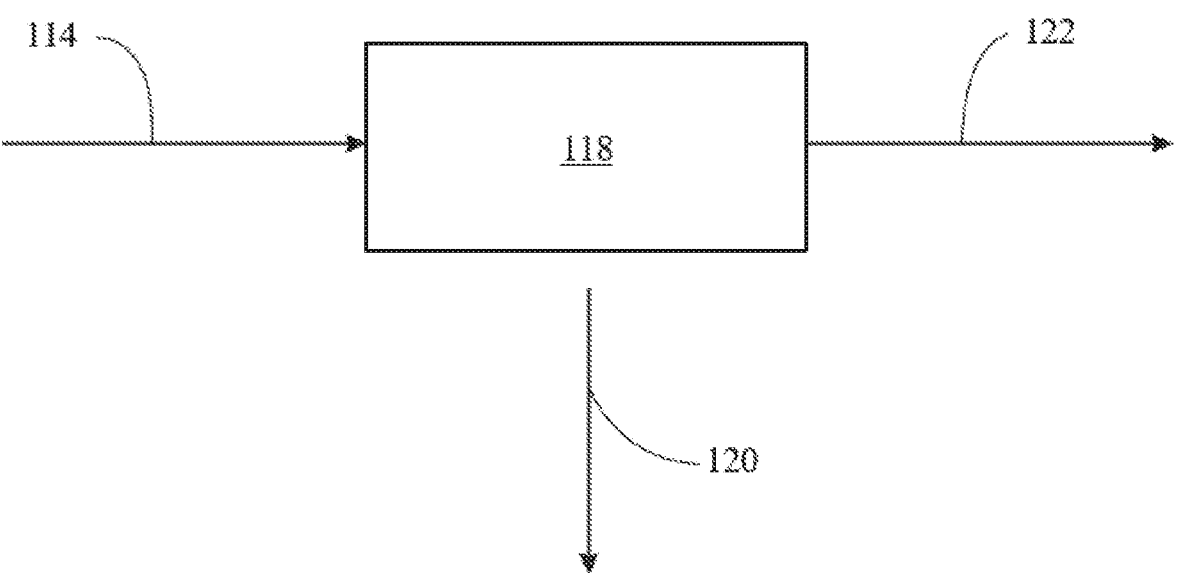
FIG. 1C is a schematic diagram of an example separation unit that can be implemented in the system of FIG. 1A.

In another aspect of the present disclosure, acetic acid produced in the oxidative dehydrogenation of ethane process can be recovered and recycled for addition to the feed stream 102 and/or the purified feed stream 108. As shown in FIG. 1C, the product stream 114 may undergo processing steps in a separation unit 118 to isolate the target product ethylene. It has been described in the art that a first processing step ideally involves removing acetic acid and water from the product stream 114, typically including cooling the product stream 114 to condense a significant portion of the acetic acid and steam which can subsequently be easily separated from the gaseous components as a liquid stream 120. The gaseous components form part of a gaseous components stream 122 including ethane, ethylene, and carbon dioxide, which may then be subjected to further processing steps, which may include separating carbon dioxide from the ethane and ethylene, followed by separation of ethane from ethylene. Isolated ethane can be recycled to form part of the feed stream 102 and/or the purified feed stream 108 (not shown). Cooling and separation of acetic acid from the product stream 114 can be non-dilutive, for example, by passing the product stream 114 through a heat exchanger. Cooling and separation of acetic acid from the product stream 114 can be dilutive, for example, by introducing the product stream 114 into a quench tower where cold water is added to the product stream 114. A combination of methods may also be employed. Regardless of which method is used for separation (dilutive, non-dilutive, or a combination of both) the liquid stream 120 including aqueous acetic acid can be recycled for use in the feed stream 102 and/or the purified feed stream 108.

The concentration of acetic acid in the liquid stream 120 can vary depending upon the original concentration in the product stream 114 and what method or combination of methods are used for separation. For example, dilutive cooling using a quench tower will result in a much lower concentration of acetic acid due to the addition of water during quenching. A person skilled in the art would be able to determine the concentration of acetic acid in the liquid stream 120 and subsequently extrapolate how much of the liquid stream 120 can be recycled to the feed stream 102 and/or the purified feed stream 108 to provide 0.5 to 10 vol. % of acetic acid. In instances where not all of the liquid stream 120 is required to provide the desired vol. % of acetic acid in the feed stream 102 and/or the purified feed stream 108, a split fraction of the liquid stream 120 can be recycled for addition to the feed stream 102 and/or the purified feed stream 108, and the remainder may be sent for further processing, such as upgrading to glacial acetic acid, using methods known in the art. In instances where the concentration of acetic acid in the liquid stream 120 is insufficient to provide enough acetic acid to provide 0.5 vol. % to 10 vol. % in the feed stream 102 and/or the purified feed stream 108 an additional source of acetic acid can be utilized to make up the difference. As described previously, the acetic acid can be diluted with steam. The gaseous portions of the streams 102, 108, 114, and 122 have compositions outside of their respective flammability limits.

In some embodiments, the oxidative dehydrogenation unit 110 includes multiple oxidative dehydrogenation reactors. The reactors can be in a parallel flow configuration, a serial flow configuration, or a combination of these. The operating conditions (temperature and pressure) of the reactors can be adjusted to improve control of product distribution, increase net ethylene yield, reduce the amount of diluent gas used in the ODH process, or any combination of these. For example, an upstream reactor can operate at a decreased temperature in comparison to a downstream reactor, an increased temperature in comparison to the downstream reactor, or the same temperature as the downstream reactor. For example, the upstream reactor can operate at a decreased pressure in comparison to the downstream reactor, an increased pressure in comparison to the downstream reactor, or the same pressure as the downstream reactor. In embodiments where the upstream reactor operates at a decreased pressure in comparison to (or the same pressure as) the downstream reactor, the system 100 can include an ejector.

Figure 2:
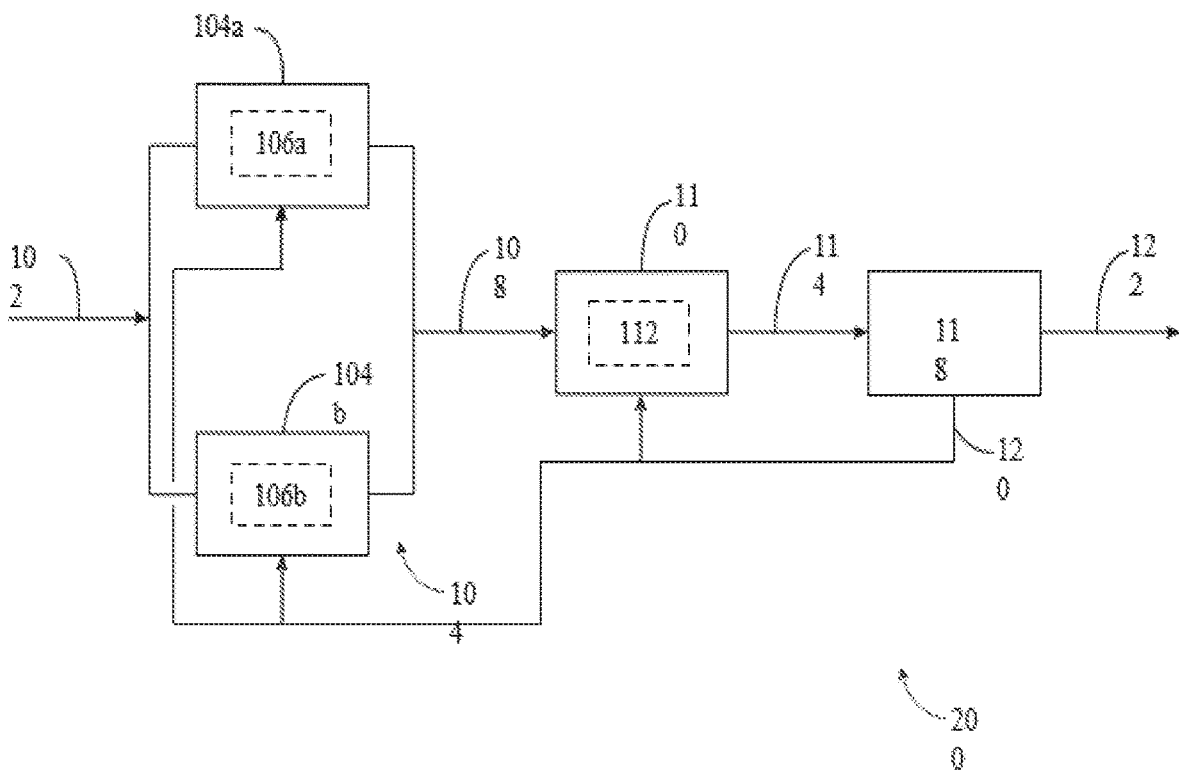
FIG. 2 is a schematic diagram of an example system for oxidative dehydrogenation.

FIG. 2 depicts a system 200 for oxidative dehydrogenation. The system 200 includes the purification unit 104, the oxidative dehydrogenation unit 110, and the separation unit 118. The purification unit 104 includes multiple purification beds 104a, 104b in a parallel flow configuration. The feed stream 102 flows to either of the purification beds 104a or 104b (for example, 104a). As the feed stream 102 flows through the first purification bed 104a, the feed stream 102 contacts the first portion 106a of the first oxidative dehydrogenation catalyst 106 operating at the first temperature. The catalyst purifies the feed stream 102 to form a purified feed stream 108. The purified feed stream 108 flows to the oxidative dehydrogenation unit 110. As the purified feed stream 108 flows through the oxidative dehydrogenation unit 110, the purified feed stream 108 contacts, in the presence of oxygen, the second oxidative dehydrogenation catalyst 112 operating at the second temperature that is greater than the first temperature. The catalyst dehydrogenates ethane in the purified feed stream 108 to form a product stream 114 that includes ethylene. The product stream 114 flows to the separation unit 118. The gaseous portion of the product stream 114 is separated to form the ethylene product 122, which can be sold or flowed to a downstream process for further processing. The liquid portion of the product stream 118 is separated to form the liquid stream 120 that includes acetic acid. The liquid stream 120 can be recycled back to the oxidative dehydrogenation unit 110, the first purification bed 106a, the second purification bed 106b, or any combination of these.

Figure 3:
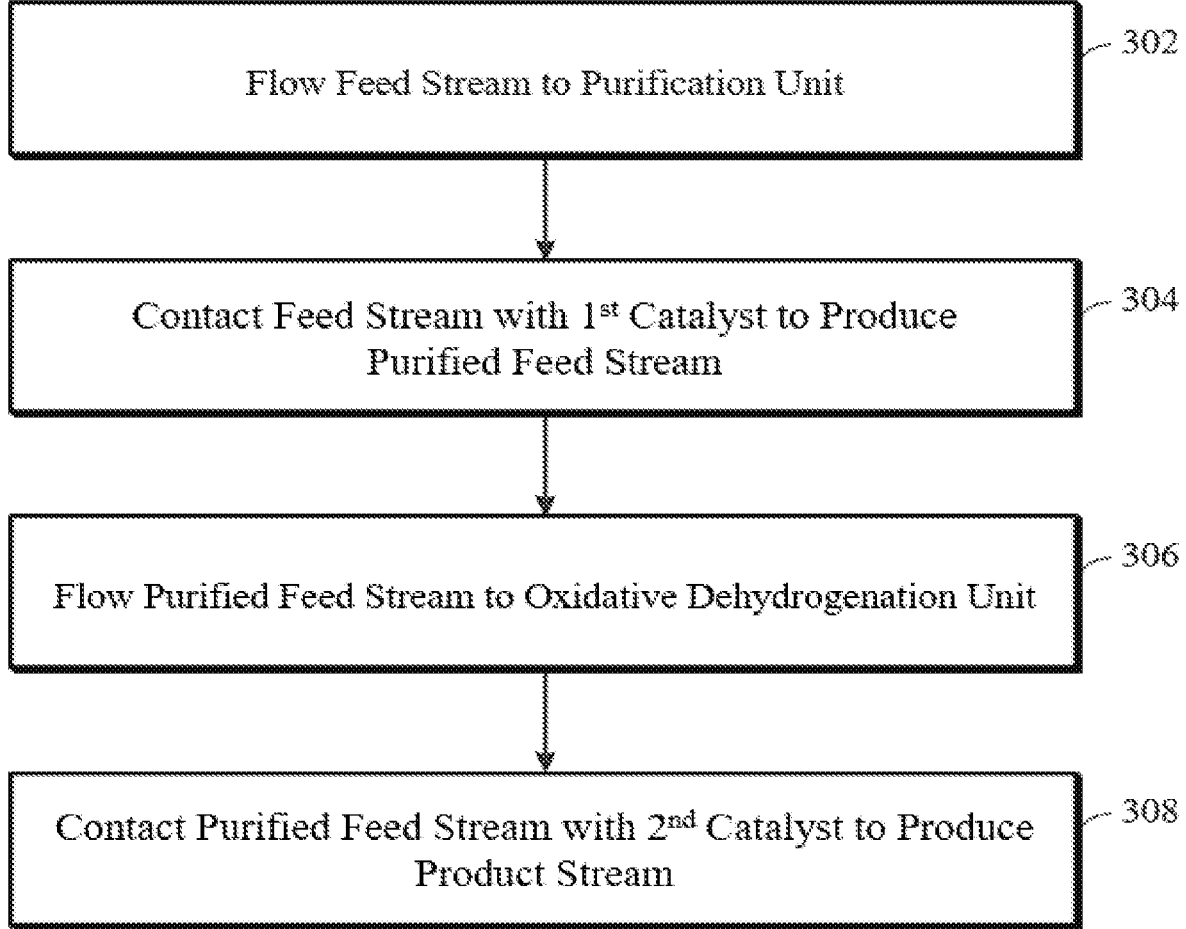
FIG. 3 is a flow chart of an example method for oxidative dehydrogenation.

Referring to FIG. 3, a method 300 can be implemented for an oxidative dehydrogenation process. The method 300 can, for example, be implemented by the system 100 of FIG. 1 or the system 200 of FIG. 2. At block 302, a feed stream (such as feed stream 102) is flowed to a purification unit (such as purification unit 104). The purification unit 104 includes a first oxidative dehydrogenation catalyst (such as oxidative dehydrogenation catalyst 106). At block 304, the feed stream 102 is contacted with the first oxidative dehydrogenation catalyst 106 at a first temperature to reduce a concentration of impurities in the feed stream 102. In some embodiments, the first temperature is less than about 250° C. As mentioned previously, the feed stream 102 includes ethane. The feed stream 102 can include additional components, such as oxygen, acetic acid, and/or an inert diluent. Contacting the feed stream 102 with the first oxidative dehydrogenation catalyst 106 at the first temperature at block 304 produces a purified feed stream (such as purified feed stream 108). In some embodiments, the purification unit 104 operates adiabatically.

At block 306, the purified feed stream 108 is flowed to an oxidative dehydrogenation unit (such as oxidative dehydrogenation unit 110). The oxidative dehydrogenation unit 110 includes a second oxidative dehydrogenation catalyst (such as oxidative dehydrogenation catalyst 112). At block 308, the purified feed stream 108 is contacted with the second oxidative dehydrogenation catalyst 112 in the presence of oxygen at a second temperature to dehydrogenate ethane in the purified feed stream 108. The second temperature at block 308 is greater than the first temperature at block 304. In some embodiments, the second temperature is greater than about 300° C. Contacting the purified feed stream 108 with the second oxidative dehydrogenation catalyst 112 at the second temperature at block 308 produces a product stream (such as product stream 114). As mentioned previously, the product stream 114 includes ethylene. The product stream 114 can include additional components, such as unreacted ethane, water, acetic acid, carbon monoxide, carbon dioxide, and/or inert diluent.

In some embodiments, the product stream 114 is flowed to a separation unit (such as separation unit 118), and is separated into an ethylene product 122 and a liquid stream 120. In some embodiments, the liquid stream 120 is recycled to the purification unit 104, the oxidative dehydrogenation unit 110, or both.

EXAMPLES

Figure 4:
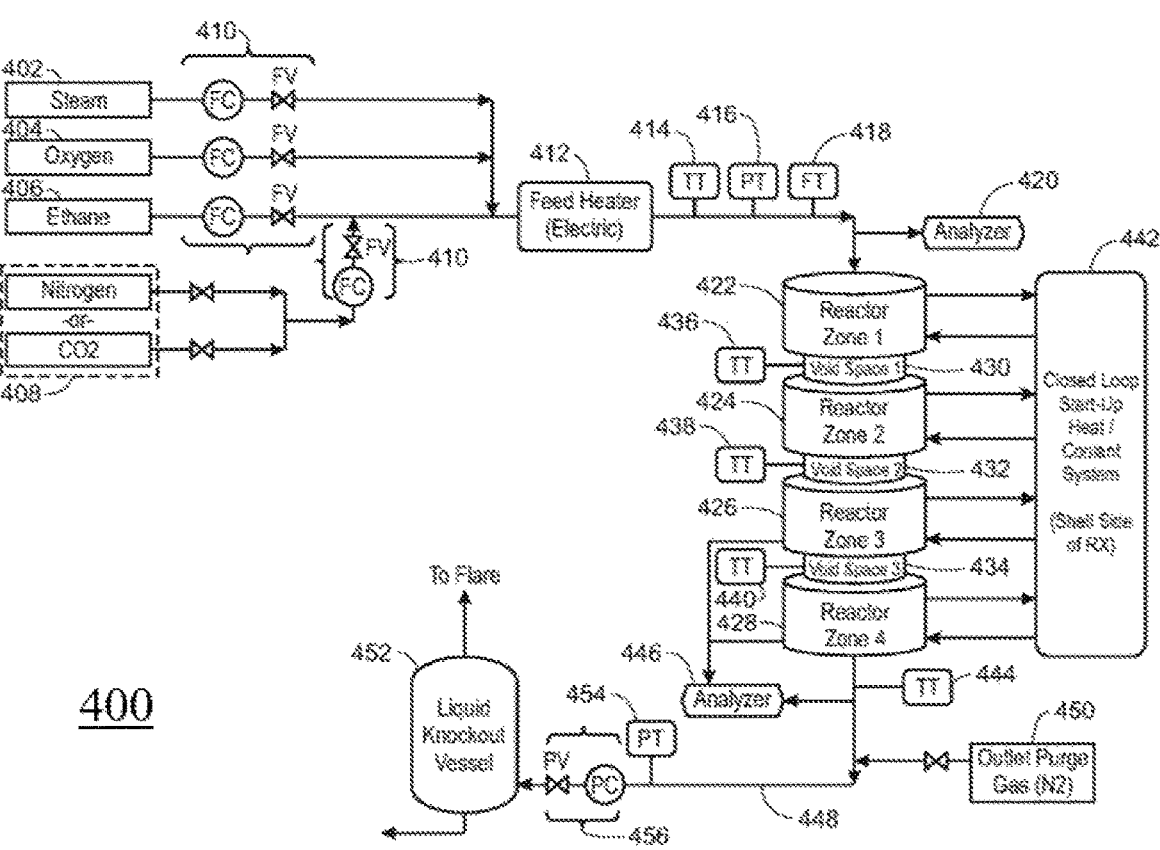
FIG. 4 is a schematic diagram of an experimental system for oxidative dehydrogenation.

The following examples are merely illustrative of the subject matter of this disclosure and are not intended to be limiting. FIG. 4 depicts a simplified block flow diagram of a reactor system 400 used in the examples described below. Reactor system 400 includes several feed streams including a steam feed stream 402, an oxygen feed stream 404, an ethane feed stream 406, and an inert gas feed stream 408. The inert gas feed stream 408 may include nitrogen, $CO_2$, or a mixture thereof. The pressure and temperature for the steam feed stream 402 ranged from about 1150 to about 1200 kPag and from about 190 to about 230° C., respectively. The pressure for oxygen feed stream 404 was about 600 kPag at ambient temperature, with a 93 vol. % purity. The pressure for ethane feed stream 406 was about 700 kPag at ambient temperature. The pressure for nitrogen feed stream was about 680 kPag at ambient temperature. The pressure for $CO_2$ feed stream 408 was about 700 kPag at ambient temperature.

As used herein, the temperature of the atmosphere in the operational environment for the scale-up reactor system 400 is at ambient temperature, e.g., without further heating or cooling. Generally, ambient temperature outdoors will vary depending upon the time of year, for example, from about −20° C. to about 25° C. However, the scale-up reactor system 400 was situated inside a test building, with a relatively stable ambient temperature of about 25° C. The ambient temperature may affect the molar amounts of the feeds added to the scale-up reactor system 400.

The addition of the each of the feed streams 402, 404, 406, and 408 was controlled by a flow controller system 410, which includes a flow controller (FC), for example, including a mass flow meter, and a flow control valve (FV). The feed streams 402, 404, 406, and 408 are blended upstream of a feed preheater 412. The feed preheater 412 is a 9 kW electric heater, with a maximum operating temperature of 375° C. A number of measurements are taken downstream of the feed preheater 412, for example, by a temperature transmitter (TT) 414, a pressure transmitter (PT) 416, a flow transmitter (FT) 418, and an analyzer 420. In some embodiments, the analyzer 420 is a gas chromatography (GC) system that may use a flame ionization detector (FID) detector, a thermal conductivity detector (TCD), a mass spectrometer, and the like. In some embodiments, the analyzer 420 incudes gas specific sensors, such as a $CO_2$ sensor, a CO sensor, and a light hydrocarbon sensor. In various embodiments, the analyzer 420 takes a regular sample from the flow from the feed preheater 412 and determines the levels of gases in the flow, including, for example, $CO_2$, CO, ethane, ethylene, $O_2$, and others.

The gas chromatography system used in the scale-up reactor system 400 was a Siemens Maxum Edition II Process Gas Chromatograph. A sample was analyzed every 150 seconds. Up to four different sample locations were routed to the same GC and analyzed in sequence. However, the most common configuration had samples from two different locations alternating through the GC such that a new result was obtained for each sample location every 300 seconds. As used in these experiments, the gas chromatography system used a series of different columns in sequence, including a 5A mol sieve Hayesep, and a Shincarbon A thermistor detector is used for the key components, such as $CO_2$, CO, oxygen, and hydrocarbons, and a flame photometric detector for trace $H_2S$.

The scale-up reactor system 400 includes four zones 422, 424, 426, and 428. The first two zones, zone 1 (422) and zone 2 (424) are about 6.7 L in volume, while the remaining zones, zone 3 (426) and zone 4 (428), are about 20.5 L in volume. Each of the zones 422, 424, 426, and 428 are separated by a void space 430, 432, and 434, respectively. The void spaces 430, 432, and 434 are each about 15 L in volume. Further, each of the void spaces 430, 432, and 434 are instrumented with a TT 436, 438, and 440 to measure the temperature of the material leaving the corresponding reactor zones 422, 424, and 426.

A temperature control system 442 is used to flow a temperature exchange media, Syltherm 800, through the shell side of the reactor zones 422, 424, 426, and 428. The temperature exchange media was used to control the temperature of the reactor zones by adding or removing heat. The maximum temperature of the Syltherm 800 used for the scale-up reactor system 400 is 360° C.

A final TT 444 is located after the reactor zone 4 (428). Further, a second analyzer 446 is coupled into the outlet line 448 to determine the gas composition. The second analyzer 446 also has sample lines that can take samples from reactor zone 3 (426) and reactor zone 4 (428). The outlet line 448 is coupled to an outlet purge gas supply 450 to purge any materials from the outlet line 448 to a knockout vessel 452 for disposal. A pressure transmitter (PT) 454 is used with a pressure controller 456 to hold a back pressure on the reactor zone 4 (428).

Reactor zones 1 (422) and 2 (424) were operated at low temperature (between 200° C. and 250° C.) to mimic the purification unit 104. Reactor zones 3 (426) and 4 (428) were operated at high temperature (above 300° C.) to mimic the oxidative dehydrogenation unit 110. Table 1 provides the loaded catalyst weight in each reactor zone.

TABLE 1

| Catalyst Loading | |
| --- | --- |
| Reactor Zone | Catalyst Weight (grams) |
| 1 | 5,635 |
| 2 | 5,600 |
| 3 | 18,762 |
| 4 | 19,007 |

A 9 kW electric heater (capable of providing a maximum temperature of 375° C.) heated the feed before it entered reactor zone 1.

After completion of the testing which spanned about 4.5 months, the catalysts from the 4 zones were unloaded. The spent catalyst from the 4 zones were characterized by inductively coupled plasma mass spectrometry (ICP-MS) to determine accumulation of feed impurities deposited on the catalyst. The ICP-MS results are provided in Table 2. The main four elements of the catalyst (Mo, V, Nb, and Te) remained basically unchanged (both in relative and absolute quantities). B and Na were observed as impurities deposited on the catalyst surface. Further, it was observed that the concentration of B and Na in reactor zone 1 (Samples 1 and 2) were at least about 2 times the concentration of these elements in reactor zones 2-4. The observed discrepancy between B and Na content between Samples 1 and 2 may imply the lack of uniformity of deposition of these elements on the catalyst surface. For example, there may be a higher uptake of impurities in the vicinity of the inlet of reactor zone 1 as opposed to the outlet of reactor zone 1. From these results, it was concluded that the catalyst in reactor zone 1 served as a purification bed and removed most of the B and Na feed impurities before the feed traveled to the downstream reactor zones 2-4.

TABLE 2

ICP-MS Results for Catalysts from Reactor Zones 1-4

| | Impurity on Catalyst Surface (ppmw) | | Main Elements in Catalyst Composition (ppmw) | | | |
|---|---|---|---|---|---|---|
| Sample | B | Na | V | Nb | Mo | Te |
| Sample 1 from Zone 1 | 1,198 | 6,864 | 34,400 | 31,930 | 193,800 | 38,600 |
| Sample 2 from Zone 1 | 1,192 | 1,477 | 30,030 | 32,780 | 176,100 | 37,610 |
| Sample from Zone 2 | 161 | 828 | 33,760 | 32,540 | 190,400 | 37,200 |
| Sample from Zone 3 | 212 | 344 | 32,050 | 28,610 | 184,400 | 35,020 |
| Sample from Zone 4 | 598 | 519 | 33,640 | 31,810 | 194,300 | 36,440 |

The spent catalyst from reactor zone 1 was then tested in ethane conversion under oxidative dehydrogenation conditions in comparison to fresh catalyst. The results of this test are provided in Table 3. The results exhibited a 9° C. increase in reaction temperature for spent catalyst from reactor zone 1 in comparison to fresh catalyst. The change in ethylene selectivity and yield was relatively low. Yield was measured by ethane conversion multiplied by ethylene selectivity, divided by 100%. From these results, it was inferred that spent catalyst from reactor zone 1 underwent partial deactivation, which may be attributed to the deposition of B and Na on the spent catalyst.

TABLE 3

Catalyst Activity for Spent Catalyst from Zone 1 vs. Fresh Catalyst

| Catalyst | Temperature at 35% Ethane Conversion (° C.) | Ethylene Selectivity at Temperature (C-atom %) |
|---|---|---|
| Fresh Catalyst | 370 | 90 |
| Spent Catalyst from Zone 1 | 379 | 94 |

Green oil fouling was observed in the ethane feed line. Green oil is a term for oligomerized long-chain hydrocarbons. Green oils are end products of undesirable polymerization reactions that can take place over the catalyst surface area and therefore may partially deactivate the catalyst. An elemental analysis of a sample of the green oil fouling was performed, and the results of the analysis are provided in Table 4. From the results, it was concluded that there was no water present in this green oil sample. The presence of 0.5 wt. % O may be attributed to the potential presence of methanol in the feed stream, which may have resulted from the injection of methanol in upstream equipment.

TABLE 4

CHO Analysis of Green Oil Sample
Collected from Ethane Feed Line

| Element | Quantity (weight %) |
|---|---|
| C | 87 ± 0.22 |
| H | 13 ± 0.20 |
| O | 0.5 ± 0.037 |

Simulated distillation gas chromatography (SimDis GC) was performed on the sample of the green oil fouling, and the results are provided in Table 5. The results show that the bulk of the green oil sample consisted of C9-C24 oligomers (about 98 wt. %). The balance was in a range of C5-C9 oligomer and C24-C40 oligomers. These results confirm the likelihood that no water was present in the sample. The SimDis GC results in Table 5 are in good agreement with the CHO analysis results in Table 4.

TABLE 5

SimDis GC Analysis of Green Oil Sample
Collected from Ethane Feed Line

| Hydrocarbon Carbon Range | Weight % |
|---|---|
| C5-C6 | 0.016 |
| C6-C7 | 0.07 |
| C7-C8 | 0.34 |
| C8-C9 | 0.53 |
| C9-10 | 3.21 |
| C10-C11 | 3.96 |
| C11-C12 | 18.8 |
| C12-C14 | 29.5 |
| C14-C15 | 8.99 |
| C15-C16 | 8.65 |
| C16-C17 | 5.24 |

TABLE 5-continued

| SimDis GC Analysis of Green Oil Sample Collected from Ethane Feed Line | |
| --- | --- |
| Hydrocarbon Carbon Range | Weight % |
| C17-C18 | 4.95 |
| C18-C20 | 6.49 |
| C20-C24 | 7.96 |
| C24-C28 | 0.67 |
| C28-C32 | 0.13 |
| C32-C36 | 0.14 |
| C36-C40 | 0.16 |

To investigate the efficacy of using acetic acid to remove B and Na impurities from the catalyst surface (that is, regenerate the catalyst), three different aqueous acetic acid solutions were prepared (1 wt. %, 10 wt. %, and 25 wt. %, balance deionized water). For each solution, a spent catalyst pellet from reactor zone 1 was collected and split in half. The first half was submerged in 10 milliliters of the acid solution for 1 hour with manual agitation every 15 minutes at ambient conditions. The submerged half was removed and dried at 120° C. in an oven for 3 days. The second half was left untreated as a control. The samples were tested by ICP-MS to determine reduction in B and Na on the catalyst surface, and the results are provided in Table 6. Using the 25 wt. % acetic acid solution, a reduction of 20% of Na from the surface of the spent catalyst was observed. Lower concentrations of acetic acid did not appear to have an effect on removing Na from the surface of the spent catalyst. Acetic acid, regardless of concentration, did not appear to have an effect on removing B from the surface of the spent catalyst. The main four elements of the catalyst (Mo, V, Nb, and Te) remained basically unchanged (both in relative and absolute quantities) by the acetic acid wash, regardless of concentration.

INDUSTRIAL APPLICABILITY

The present disclosure relates to a process for oxidative dehydrogenation of ethane that includes preliminary feed purification.

The invention claimed is:

1. A process for oxidative dehydrogenation of ethane comprising:
flowing a feed stream comprising ethane to a purification unit comprising a first oxidative dehydrogenation catalyst;
contacting the feed stream with the first oxidative dehydrogenation catalyst at a first temperature to reduce a concentration of impurities in the feed stream to produce a purified feed stream;
flowing the purified feed stream to an oxidative dehydrogenation unit comprising a second oxidative dehydrogenation catalyst; and
contacting the purified feed stream with the second oxidative dehydrogenation catalyst in the presence of oxygen at a second temperature greater than the first temperature to dehydrogenate ethane to produce a product stream comprising ethylene.

2. The process according to claim 1, wherein the first temperature is less than about 250 degrees Celsius (° C.).

3. The process according to claim 2, wherein the second temperature is greater than about 300° C.

4. The process according to claim 1, wherein the first oxidative dehydrogenation catalyst and the second oxidative dehydrogenation catalyst have the same composition.

5. The process according to claim 1, wherein the purification unit operates adiabatically.

6. The process according to claim 1, wherein the purification unit comprises a first purification bed and a second purification bed in a parallel flow configuration.

7. The process according to claim 6, wherein a first portion of the first oxidative dehydrogenation catalyst is disposed within the first purification bed, and a second

TABLE 6

| | | Pellet 1 25 wt. % AcOH No wash (control) | Pellet 1 25 wt. % AcOH Washed | Pellet 2 10 wt. % AcOH No wash (control) | Pellet 2 10 wt. % AcOH Washed | Pellet 3 1 wt. % AcOH No wash (control) | Pellet 3 1 wt. % AcOH Washed |
| --- | --- | --- | --- | --- | --- | --- | --- |
| ICP-MS Results for Spent Catalyst from Reactor Zone 1 Before and After Acetic Acid Wash | | | | | | | |
| Catalyst Main Elements | | | | | | | |
| Mo | ppm | 177,700 | 177,500 | 172,800 | 177,700 | 189,800 | 170,800 |
| V | ppm | 32,760 | 36,200 | 31,530 | 33,560 | 34,640 | 39,970 |
| Nb | ppm | 33,230 | 37,020 | 32,940 | 34,900 | 35,620 | 34,710 |
| Te | ppm | 49,480 | 71,820 | 43,350 | 48,280 | 59,090 | 62,150 |
| Catalyst Main Elements Relative to Mo | | | | | | | |
| Mo | mass ratio | 1.00 | 1.00 | 1.00 | 1.00 | 1.00 | 1.00 |
| V | mass ratio | 0.18 | 0.20 | 0.18 | 0.19 | 0.18 | 0.20 |
| Nb | mass ratio | 0.19 | 0.21 | 0.19 | 0.20 | 0.19 | 0.20 |
| Te | mass ratio | 0.28 | 0.40 | 0.25 | 0.27 | 0.31 | 0.36 |
| Catalyst Surface Impurities | | | | | | | |
| B | ppm | 1,731 | 1,787 | 531.8 | 1,055 | 4,617 | 4,941 |
| Na | ppm | 2,644 | 2,140 | 231.9 | 1,035 | 3,355 | 4,176 | portion of the first oxidative dehydrogenation catalyst is disposed within the second purification bed.

8. The process according to claim 7, wherein:

flowing the feed stream to the purification unit comprises flowing the feed stream to the first purification bed; and contacting the feed stream with the first oxidative dehydrogenation catalyst comprises contacting the feed stream with the first portion of the first oxidative dehydrogenation catalyst disposed within the first purification bed.

9. The process according to claim 8, comprising regenerating the second portion of the first oxidative dehydrogenation catalyst disposed within the second purification bed while the feed stream is flowed to the first purification bed.

10. The process according to claim 9, wherein regenerating the second portion of the first oxidative dehydrogenation catalyst comprises contacting the second portion of the first oxidative dehydrogenation catalyst with acetic acid.

11. The process according to claim 9, wherein the product stream comprises acetic acid, and the process comprises:

separating the acetic acid from the product stream;

recycling the acetic acid separated from the product stream to the second purification bed; and contacting the second portion of the first oxidative dehydrogenation catalyst disposed within the second purification bed with the recycled acetic acid.

12. The process according to claim 8, comprising flowing an oxidizing stream comprising oxygen to the second purification bed while the feed stream is flowed to the first purification bed.

\* \* \* \* \*